United States Patent [19]

Pollack et al.

[11] Patent Number: 4,897,380

[45] Date of Patent: * Jan. 30, 1990

[54] METHOD AND COMPOSITION FOR RELIEVING DIETARY-RELATED DISORDERS

[76] Inventors: Robert L. Pollack, 8442 Chippewa Rd., Philadelphia, Pa. 19128; Lawrence Durst, 5 W. 5th St., Bridgeport, Pa. 19405

[*] Notice: The portion of the term of this patent subsequent to Jan. 27, 2004 has been disclaimed.

[21] Appl. No.: 7,121

[22] Filed: Jan. 27, 1987

Related U.S. Application Data

[63] Continuation-in-part of Ser. No. 771,325, Aug. 30, 1985, Pat. No. 4,639,465.

[51] Int. Cl.$^4$ .................. A61K 31/40; A61K 31/70; A61K 31/435
[52] U.S. Cl. ...................... 514/23; 514/277; 514/419
[58] Field of Search .................... 514/23, 419, 277

[56] References Cited

PUBLICATIONS

"A New Activator Protein That Activates Tryptophan 5–Monooxygenase and Tyrosine 3–Monooxygenase in the Presence of $Ca^{2+}$–, Calmodulin–Dependent Protein Kinase", Takashi Yamauchi et al., The Journal of Biological Chemistry, vol. 256, No. 11, pp. 5404–5409, Jun. 10, 1981.

"The Respective Roles of Tryptophan Uptake and Tryptophan Hydroxylase in the Regulation of Serotonin Synthesis in the Central Nervous System", J. Physiol., Paris, 1981, vol. 77, pp. 269–279, Symposium the Serotoninergic Neuron CNRS, Marseille, Jul. 9–14, 1980, M. Hamon et al.

"$Ca^{2+}$–Guanine Nucleotide Interactions in Brain Membranes. I. Modulation of Central 5–Hydroxytryptamine Receptors in the Rat", M. Mallat et al., Journal of Neurochemistry, 1982, pp. 151–161.

"Serotonin and Lysergic Acid Diethylamide Binding in Rat Brain Membranes: Relationship to Postsynaptic Serotonin Receptors", James P. Bennett, Jr. et al., Molecular Pharmacology, vol. 12, pp. 373–389, 1976.

Primary Examiner—Stanley J. Friedman
Attorney, Agent, or Firm—Ratner & Prestia

[57] ABSTRACT

A composition for treating physiological disorders responsive to treatment with the neurotransmitter serotonin includes L-tryptophan, fructose, niacinamide, pyridoxine, calcium ascorbate, copper gluconate and magnesium oxide. Each ingredient either promotes the transport of L-tryptophan from the blood plasma across the blood-brain barrier into the brain, or promotes the synthesis of serotonin from L-tryptophan.

14 Claims, No Drawings

METHOD AND COMPOSITION FOR RELIEVING DIETARY-RELATED DISORDERS

This is a continuation-in-part application of application Ser. No. 771,325, filed Aug. 30, 1985, now U.S. Pat. No. 4,639,465.

Reference is made to the copending patent application of Robert L. Pollack, application Ser. No. 787,502, filed Oct. 15, 1985 and to the copending patent application of John V. Cappello, application Ser. No. 825,196, filed Feb. 3, 1986.

BACKGROUND OF THE INVENTION

1. FIELD OF THE INVENTION

This invention relates generally to a dietary supplement for relieving physiological disorders and particularly relates to a composition which promotes the production of serotonin within the brain.

2. DESCRIPTION OF PRIOR DEVELOPMENTS

Attention has recently turned to nontraditional methods and compositions for treating various physiological disorders in an effort to provide relief in those instances where standard techniques have proven ineffective and where it is desired to avoid the undesirable side effects of conventional pharmaceutical compositions. One approach has been to attempt to provide relief through dietary supplementation of L-tryptophan (tryptophan).

Once within the brain, neurons convert tryptophan into the neurotransmitter serotonin. It has been found that an increase of tryptophan in the brain increases the brain's production of serotonin. Brain levels of serotonin have been shown to be linked to sleep, appetite, depression, and pain threshold. Disturbances in the brain causing reduced levels of serotonin have been linked to clinical (endogenous) depression, insomnia, excessive appetite, weight gain and lowered pain threshold.

While treatment of such disorders with supplemental tryptophan has heretofore produced positive results, there has been a wide range in the degree of relief achieved. Some patients appear to respond more favorably to such treatment than others for no previously known reason. Thus, complete relief has not consistently been assured by prior dietary tryptophan supplements. It is believed that these conventional supplements lack a complete combination of ingredients necessary to ensure the maximum relief achievable with every patient through tryptophan supplementation.

It is known that dietary supplementation of tryptophan increases the blood level of tryptophan and facilitates the passage of tryptophan across the blood-brain barrier into the brain. The increased amount of tryptophan in the brain permits a greater amount of tryptophan to be converted to serotonin.

In order for tryptophan to be converted to serotonin in the brain, it must cross a separating mechanism that exists between the blood vessels and the brain. To reach the brain, tryptophan requires a carrier transport mechanism in the form of a carrier protein which, literally, carries tryptophan across this very selective blood-brain barrier and into the brain. Not only is tryptophan carried by this transport mechanism, but other selected amino acids, called large neutral amino acids (LNAAs), are carried as well.

Tryptophan not only has to compete with the LNAAs for access to the transport carrier mechanism, it also has a lower affinity for the carrier system than does the LNAAs. To compound this situation further, tryptophan in foods is generally present in lower amounts than the LNAAs—particularly in animal proteins. All of these factors contribute to the amount of tryptophan that actually gets through to the brain, to be finally converted to serotonin.

There are numerous conditions, improper diet constitutes one of them, that can interfere with, and decrease, the amount of tryptophan that normally passes through the blood-brain barrier into the brain each day. This comes about when the ratio of tryptophan to LNAAs in the blood reaching the brain is lower than normal. This means that the number of molecules of tryptophan present at the blood-brain barrier is much smaller than the number of molecules of LNAAs present at the same blood-brain barrier. The LNAAs overwhelm the tryptophan such that very little tryptophan is provided passage into the brain as compared to the number of LNAAs that are provided passage.

In the attempt to correct this improper tryptophan/LNAA ratio, it was found that increasing the total protein intake obtained from normal dietary sources, in order to add more tryptophan to the system, results, paradoxically, in an even greater decrease in the amount of tryptophan reaching the brain. This is so because there are usually more LNAAs than there is tryptophan in food. Experimental studies have established the fact that increasing the amount of protein as food, in order to improve the tryptophan/LNAA ratio, only makes the tryptophan/LNAA ratio worse because of the greater intake of the LNAAs over the intake of the tryptophan.

With less tryptophan getting into the brain, less serotonin is formed, and a wide variety of disorders, including those noted above, begin to manifest themselves. Because these disorders stem from a biochemical imbalance involving the tryptophan-serotonin relationship, they cannot be corrected by any conventional medication. Such disorders are unmanageable by any conventional drug therapy because the drug does not address itself to the correction of this specific biochemical imbalance.

Accordingly, a need exists for a method and composition for transporting an effective dose of tryptophan across the blood-brain barrier into the brain and for promoting the conversion of tryptophan into serotonin. Moreover, a need exists for a composition which provides all the ingredients necessary to achieve the maximum relief possible through dietary supplementation of tryptophan.

SUMMARY OF THE INVENTION

The present invention has been designed to provide the proper dietary supplementation of a tryptophan-based composition which will relieve clinical depression, promote sleep, reduce appetite and relieve chronic pain.

The administration of pure tryptophan will: (1) help to improve the ratio of blood tryptophan to blood LNAAs, (2) help to increase the amount of tryptophan that will enter the brain, and (3) help to increase the serotonin level and relieve any one or all disorders stemming from inadequate production of serotonin.

The oral administration of tryptophan under proper dietary conditions thus provides a supplementary intake of this particular amino acid which helps to correct an improper tryptophan/LNAA ratio. The dietary supplementation of the tryptophan-based composition described below, combined with an adjusted protein, low fat, higher carbohydrate intake, results in a significant reduction in any one or all unpleasant symptoms experienced by patients having low or insufficient brain levels of serotonin. When administered as an anorectic, the composition significantly reduces intake of all calorie laden nutrients including protein, fats and carbohydrates, thereby serving as an effective aid in any weight control program.

A major aspect of the present invention is specifically directed to the addition of calcium, magnesium and ascorbic acid to a tryptophan-based composition so that both the level of serotonin within the brain is increased and the quality and strength of the nerve signals or impulses transmitted by this neurotransmitter is improved and strengthened.

In order to appreciate the specific selection and combination of ingredients described below, a brief description of the biochemical processes by which tryptophan is converted into serotonin is of value.

Generally, serotonin is produced within brain membranes by a process involving the interaction of the amino acid L-tryptophan with the enzyme trypophan hydroxylase. More particularly, two separate enzymatic steps are necessary for the synthesis of serotonin (5-HT) from its natural precursor tryptophan. The first step involves the conversion of tryptophan into 5-hydroxytryptophan (5-HTP) via interaction with the enzyme tryptophan hydroxylase. The second step involves the decarboxylation of 5-HTP into 5-HT via aromatic amino acid decarboxylase.

It is the first step which is believed to present the greatest hurdle in the conversion of tryptophan to serotonin. Moreover, it is believed that this first step primarily affects the amount of serotonin produced within the brain. Accordingly, it is the first enzymatic step on which the present invention concentrates.

As stated, tryptophan must first be converted to 5-HTP by tryptophan hydroxylase. However, only a special activated form of tryptophan hydroxylase will bring about this conversion. This activated form is a phosphorylated form of tryptophan hydroxylase which is produced through the action of a calcium-dependent protein kinase. It is calcium which stimulates the kinase to phosphorylate the tryptophan hydroxylase. Thus, the addition of calcium to the tryptophan composition ensures the adequate presence of calcium required to initiate the conversion of tryptophan to serotonin.

Another factor in the synthesis or conversion of tryptophan into serotonin involves the hydroxylation of tryptophan by the phosphorylated tryptophan hydroxylase. The rate-limiting step in the synthesis of serotonin is the hydroxylation step which is catalyzed by tryptophan hydroxylase. Once tryptophan crosses the blood-brain barrier into the brain, the tryptophan bonds with nerve membranes on serotoninergic neurons. At this point the tryptophan undergoes hydroxylation by accepting an OH group from the activated enzyme tryptophan hydroxylase, a copper-protein enzyme, which is present within the brain.

The hydroxylation of tryptophan is believed to involve the reduction of the calcium/kinase-activated tryptophan hydroxylase copper atoms and the reduction of a presently unknown enzyme group X also present on the enzyme. Thus, by providing supplemental ascorbic acid and copper according to the invention, the hydroxylation of tryptophan into 5-HTP is further facilitated. The reduction of the tryptophan hydroxylase takes place by the successive addition of single electrons to its copper atoms and to the enzyme group X from ascorbic acid. That is, tryptophan hydroxylase is a copper-protein complex that uses ascorbic acid as a reducing agent. Thus, by providing supplemental ascorbic acid and copper according to the invention, the hydroxylation of tryptophan into 5-HTP is further facilitated.

In short, calcium initially stimulates kinase to activate (phosphorylate) tryptophan hydroxylase. The tryptophan is then hydroxylated by the activated or phosphorylated tryptophan hydroxylase through reduction of copper via electron transfers from ascorbic acid.

To further ensure the efficacy of serotonin in relieving physiological disorders, magnesium is added to the composition, preferably along with calcium, to increase the bond strength between serotonin and the nerve membranes as well as to increase the total number of binding sites available to serotonin on the brain/nerve membranes. By increasing both the strength and the number of bonds between serotonin and the nerve membranes, a stronger nerve impulse or signal is transmitted by the passage of serotonin across the nerve synapses thereby resulting in a more pronounced physiological effect leading to more pronounced relief.

It is possible that the somewhat unpredictable results achieved by prior tryptophan-based compositions may be attributable to a lack of ascorbic acid, calcium and/or magnesium available in the patient's brain for the conversion of tryptophan to serotonin.

It is therefore an object of the invention to provide a method and composition for relieving physiological disorders through dietary supplementation of tryptophan in combination with other ingredients which facilitate the brain's synthesis of serotonin.

Another object is to efficiently transport tryptophan across the blood-brain barrier so that an effective relief-yielding quantity of serotonin is produced within the brain.

Still another object of the invention is to provide a method and composition for promoting the conversion of tryptophan to serotonin within the brain.

Yet another object is to facilitate the activation of the enzyme tryptophan hydroxylase which, when activated, converts tryptophan into a precursor of serotonin, namely, 5-hydroxytryptophan.

Still another object is to increase the total number of available serotonin binding sites on brain membranes.

Another object is to increase the specific binding of serotonin to all available binding sites on brain membranes by increasing the bond strength between serotonin and nerve axons.

A particularly effective composition has been found to include tryptophan, calcium, magnesium, ascorbic acid, niacinamide, pyridoxine, and a carbohydrate such as a sugar. A most effective sugar has been found to be fructose, which yields a steadily metered release of insulin into the blood. A preferred single source of both calcium and ascorbic acid is available as calcium ascorbate.

DETAILED DESCRIPTION OF THE PREFERRED EMBODIMENTS

As briefly stated above, there are eight operative ingredients which, when combined according to the invention, yield an effective composition for promoting the transport of tryptophan from the blood plasma into the brain and for promoting the synthesis of serotonin from tryptophan within the brain. High brain levels of serotonin have been shown to increase one's pain threshold level, decrease appetite, relieve depression and promote sleep. The primary ingredient, tryptophan, may be provided in any amount ranging from about 50 milligrams per dosage up to about 12 grams per dosage. However, a preferred dosage range has been found to extend from about 50 milligrams to one gram per dosage, particularly if the dosage is repeated several times daily. A preferred dosage schedule during waking hours may range from once an hour to once every three or four hours.

In addition to the primary ingredient tryptophan, any one, several or all of the following seven additional ingredients may be provided to facilitate tryptophan transport into the brain and/or to promote conversion of tryptophan into serotonin. These additional ingredients may either be directly combined with tryptophan and formed as a tablet or capsule, or may be coadministered as separate ingredients. Of course, the dosage schedule of each additional ingredient would be the same as that for the tryptophan.

The first supplemental ingredient is calcium, preferably in the form of calcium ascorbate provided in single dosage amounts ranging from 1 to 500 milligrams. Calcium may alternatively be provided as any one or any combination of the following salts of calcium within a single dosage weight range of 1 to 500 milligrams:

| | |
|---|---|
| calcium ascorbate | calcium gluconate |
| calcium carbaspirin | calcium glycerophosphate |
| calcium carbonate | calcium lactate |
| calcium caseinate | calcium pantothenate |
| calcium chloride | dicalcium phosphate |
| calcium glubionate | tricalcium phosphate |
| | calcium pyrophosphate |

A most effective dosage for the above-listed salts may vary from 10 to 100 milligrams.

When a nerve cell is stimulated, one of the first events to occur is a transient but significant increase in free intracellular calcium concentrations. Concentrations of calcium also increase in the nerve cell endings upon transmission of a nerve impulse. Calcium migrates from within the neuron fibers to the outer surfaces of the cell upon nerve stimulation thereby raising the concentration of calcium at the nerve endings. This increase in calcium signals the nerve cell to release the nerve's chemical transmitter, i.e., serotonin.

Calcium does not act alone in triggering the release of serotonin. Rather, calcium stimulates the release of neurotransmitters in concert with the protein calmodulin. Calmodulin acts as an intracellular intermediary or regulator for calcium ions. As noted above, an activated form of kinase is required for the synthesis of serotonin. The calcium ions activate kinase by combining with calmodulin on serotoninergic neurons to form a calcium-calmodulin complex. Without sufficient calcium, the transmission of the nerve impulses is impeded since insufficient kinase is activated.

Calcium not only plays a crucial role in the depolarization-induced activation of tryptophan hydroxylase as previously discussed, but also aids the binding of serotonin to nerve membranes. Whereas high concentrations of monovalent cations (greater than 20 mM of Na or K) induce a significant inhibition of serotonin binding to brain membranes, millimolar concentrations of divalent cations such as calcium ($Ca^2$) and magnesium ($Mg^2$) consistently increase the specific binding of serotonin to nerve cells responsible for transmission of nerve impulses. In addition, calcium also increases the total number of specific binding sites for serotonin in brain membranes.

Accordingly, a calcium "window" exists between upper and lower limits of calcium concentrations wherein sufficient calcium is provided to activate kinase but not in excessive amounts which would inhibit the binding of serotonin on nerve membranes. By providing 1 to 500 milligrams of a calcium salt as specified, calcium concentrations will be maintained within this "window" range.

Another ingredient which is advantageously included in the dietary composition is magnesium, preferably in the form of magnesium oxide in amounts ranging from to 500 milligrams. Magnesium may also be provided as any one or any combination of the following salts of magnesium within a weight range of 1 to 500 milligrams:

| | |
|---|---|
| magnesium carbonate | magnesium oxide |
| magnesium gluconate | magnesium sulfate |
| magnesium hydroxide | magnesium trisilicate |

These salts are preferably administered in amounts ranging from 10 to 100 milligrams per dosage.

Again, millimolar concentrations of divalent cations such as $Mg^2$ and $Ca^2$ consistently increase the specific binding of serotonin to the nerve cells responsible for receipt and transmission of nerve impulses. Nerve impulses are transmitted across the nerve synapse under the control of an on-off switching mechanism. The "on" state is energized by the production of neurotransmitters including serotonin. Serotonin is produced in the nerve dendrites and travels across the synapse to the axon of an adjacent nerve cell. In order to effectively transmit the nerve signal from one nerve cell to another, serotonin must find a binding site on an adjacent axon. The presence of millimolar concentrations of magnesium not only increases the number of available binding sites for serotonin but also increases the strength of the resulting bonds between the neurotransmitters and the nerve cells. The result is a stronger and clearer transmission of nerve signals via enhanced transmission and binding of serotonin. This in turn results in more effective relief of the disorders associated with a tryptophan deficiency.

Ascorbic acid is another ingredient which is beneficial for promoting production of serotonin. Ascorbic acid is a hydrolase cofactor which is required for the hydroxylation of L-tryptophan to 5-hydroxytryptophan as outlined above. A preferred form or compound for supplemental ascorbic acid is calcium ascorbate which, when ingested, provides not only ascorbic acid but also the calcium required to initiate the phosphorylation of tryptophan hydroxylase. The weight range of the calcium ascorbate is preferably within 1 to 500 milligrams. Other suitable sources of ascorbic acid include:

| |
|---|
| sodium ascorbate |
| calcium ascorbate |
| niacinamide ascorbate |

These alternate sources of ascorbic acid should be maintained within the 1 to 500 milligram limit specified above with a preferred range of 10 to 100 milligrams per dose.

Another ingredient which is beneficial in optimizing the production of serotonin is copper, the mineral element that serves as a co-factor in the enzymatic reaction involving tryptophan hydroxylase. A preferred form or compound for supplemental copper is copper gluconate which, when ingested, provides the element copper which is essential in the formation of the active enzyme complex. The weight range of the copper is preferably within 0.1 to 100 milligrams. Other suitable sources of copper include:

---
copper sulfate
amino acid chelates of copper
---

The preferred dosage forms of these salts are in amounts of copper ranging from 0.1 to 100 milligrams of copper.

Niacinamide is another additional ingredient which may be included to promote or facilitate tryptophan transport into the brian. Niacin is an essential nutrient that the human body must have at all times. Because of niacin's importance, the body has evolved a method by which it can synthesize niacin from tryptophan. More particularly, 60 milligrams of tryptophan is used by the body to make each milligram of niacin. Studies in humans have shown that the amount of niacin the body gets from tryptophan amounts to about one-half of the total amount of niacin that the body needs each day, that is, about 13-19 mg. This means that from $(13/2 \times 60)$ mg to $(19/2 \times 60)$ mg or 390 mg to 570 mg of tryptophan is needed each day for its conversion to niacin.

In order to attempt to minimize the destruction of the supplemental tryptophan within the body via synthesis into niacin, a niacin supplement such as niacinamide or nicotinamide is included along with the tryptophan to provide the body with the pre-formed vitamin niacin. Furthermore, it has been learned that some of the beneficial effects of tryptophan in raising brain levels of serotonin may be diminished by a rapid breakdown (catabolism) by tryptophan pyrrolase. The administration of a tryptophan pyrrolase inhibitor such as niacinamide, nicotinamide or nicotinic acid inhibits such tryptophan breakdown in man. A practical dosage may range from 1 milligram to 100 milligrams with a preferred range of 5 to 25 milligrams.

The next operative ingredient of the invention is pyridoxine (vitamin $B_6$). Pyridoxine is essential in the tryptophan-serotonin conversion process and is part of the enzyme system which functions directly in the conversion of tryptophan to serotonin. That is, pyridoxine is a decarboxylase co-factor required for the decarboxylation of 5-hydroxytryptophan to serotonin. By providing the body with this vitamin at the same time that the supplemental tryptophan is administered, this important nutrient will be provided to individuals whose dietary intake may have been deficient. This will ensure efficient conversion of tryptophan to serotonin. Pyridoxine may be administered in dosages ranging from 0.5 to 50 milligrams, with a preferred range of 1 to 10 milligrams per dose.

The next ingredient is the monosaccharide sugar, fructose. Investigations have shown that dietary carbohydrate causes an increase in the relative concentration of blood tryptophan levels; i.e., the amount of tryptophan is increased relative to the amount of the interfering large neutral amino acids that compete with tryptophan for the transport carrier mechanism in the brain. Of all the blood amino acids, tryptophan is the only amino acid that is carried as an albumin-bound complex. All of the other amino acids, including the LNAAs, travel in the blood as the free amino acids.

Insulin, when elaborated into the blood stream in response to an increase in blood sugar concentration serves to drive amino acids into the body tissues while the blood courses on its way to the brain. The tryptophan-albumin complex is not affected by this insulin action, and thus remains available to reach the brain. Thus, this complex is not "lost" to the body tissues. However,, the other amino acids are removed from the blood thereby increasing the relative percentage of tryptophan in the blood. Carbohydrate intake, therefore, with its insulin-releasing action, helps to improve the tryptophan/LNAA ratio in favor of the tryptophan and increases the amount of tryptophan crossing the blood-brain barrier into the brain. Fructose is included in each capsule as a preferred source of carbohydrate to achieve this insulin/LNAA/-tryptophan effect.

Relatively modest dosages of fructose have been found sufficient to produce the desired effects. For example, dosages of fructose as little as 5 milligrams have been found to increase the effect of tryptophan in providing relief of the disorders mentioned above. A preferred dosage ranges from 25 milligrams to one gram per dosage.

While the weight percentages of each ingredient listed below could vary at least by 50% and in accordance with the amounts found to achieve an optimum effect, a preferred composition of the supplement for an effective single dosage (tablet or capsule) for a typical patient is approximately as follows:

|  | Weight in mg | % by weight (approx.) |
|---|---|---|
| L-tryptophan | 250 | 48 |
| Fructose | 125 | 24 |
| Niacinamide | 10 | 2 |
| Pyridoxine | 5 | 1 |
| Calcium ascorbate | 55 | 10.5 |
| Magnesium oxide | 55 | 10.5 |
| Copper gluconate | 15 | 4 |
| Total weight of tablet | 515 mg | 100% |

Because the above composition can be taken orally in amounts up to 10-12 capsules daily, the inclusion of the sugar, fructose, was deliberately selected rather than glucose or sucrose because of studies which indicate that the response of the body in releasing insulin into the blood is much more even with fructose than with the other sugars that were used and without any sudden insulin upsurge. Thus, fructose provides the desired predictability of insulin release needed for a constant production of serotonin which in turn is required for the satisfactory even relief of physiological disorders. Treatment of physiological disorders may be carried out according to the invention with maximum sustained or prolonged daily dosages of up to:

| L-tryptophan | 15 grams |
|---|---|
| Fructose | 20 grams |
| Niacinamide (Nicotinamide, Nicotinic Acid) | 2 grams |
| Pyridoxine | 2 grams |
| Calcium ascorbate (or any other calcium salt) | 6 grams |
| Magnesium oxide (or any other magnesium | 6 grams |

|  |  |
| --- | --- |
| salt) | |
| Ascorbic Acid (or any other acceptable ascorbate) | 6 grams |
| Copper gluconate (or any other copper salt) | 1 gram |

These maximum dosages may be administered at one time and in any combination which includes at least L-tryptophan and fructose, although lesser dosages spaced over time are preferred.

Obviously numerous modifications and variations of the present invention are possible in light of the above teachings. It is therefore to be understood that within the scope of the appended claims, the invention may be practiced otherwise than as specifically described herein. For example, other carbohydrates could be used in place of fructose without departing from the spirit of the invention.

While upper daily limits have been placed on each ingredient for prolonged use of the composition, virtually no upper limit need be maintained for any ingredient for initial or intermittent treatment of physiological disorders. It has been found that initial treatment may require five to ten times the maximum normal or sustained dosages identified above in order to accelerate initial relief. Once relief is achieved, lower dosages may be maintained according to the above-specified ranges.

Moreover, it should be noted that only tryptophan and fructose are essential to carry out the invention. The remaining ingredients are optional and may be added in any combination with the tryptophan and fructose depending upon the dietary deficiency of a particular patient. Those patients exhibiting a deficiency in any one or a combination of the remaining six ingredients may be treated only with those ingredients specifically required to overcome the patient's particular deficiency.

What is claimed is:

1. A daily dietary supplement for relieving clinical depression, promoting sleep, reducing appetite, and relieving chronic pain in a patient, comprising:
   from about 50 milligrams to about 15 grams of L-tryptophan for increasing production of serotonin within the patient's brain; and
   from about 5 milligrams to about 20 grams of fructose for producing a steady release of insulin into the patient's blood so as to increase the concentration of L-tryptophan in the patient's blood and to provide a steady and prolonged increase in the transport of L-tryptophan from the patient's blood into the patient's brain.

2. The dietary supplement of claim 1, further comprising from about one milligram to about two grams of a niacin supplement.

3. The dietary supplement of claim 1, further comprising from about 0.5 milligram to about 2 grams of pyridoxine.

4. The dietary supplement of claim 1, further comprising from about one milligram to about 6 grams of a calcium supplement.

5. The dietary supplement of claim 1, further comprising from about one milligram to about 6 grams of a magnesium supplement.

6. The dietary supplement of claim 1, further comprising from about one milligram to about 6 grams of ascorbic acid.

7. The dietary supplement of claim 1, further comprising from about 0.1 milligram to about 1 gram of copper.

8. A method for relieving clinical depression, promoting sleep, reducing appetite, and relieving chronic pain in a patient, by treatment with serotonin, comprising:
   administering to a patient from about 50 milligrams to about 50 grams of L-tryptophan to increase production of serotonin within the patient's brain; and
   administering to a patient from about 5 milligrams to about 20 grams of fructose to produce a steady release of insulin into the patient's blood so as to increase the concentration of L-tryptophan in the patient's blood and to provide a steady and prolonged increase in the transport of L-tryptophan from the patient's blood into the patient's brain.

9. The method of claim 8, further comprising:
   administering to the patient from about one milligram to about 2 grams of a niacin supplement.

10. The method of claim 8, further comprising:
    administering to the patient from about 0.5 milligram to about 2 grams of pyridoxine.

11. The method of claim 8, further comprising:
    administering to the patient from about one milligram to about 6 grams of a calcium supplement.

12. The method of claim 8, further comprising:
    administering to the patient from about one milligram to about 6 grams of a magnesium supplement.

13. The method of claim 8, further comprising:
    administering to the patient from about one milligram to about 6 grams of ascorbic acid.

14. The method of claim 8, further comprising:
    administering to the patient from about 0.1 milligram to about 1 gram of copper.

* * * * *